US011699531B2

(12) United States Patent
El Saadawi

(10) Patent No.: US 11,699,531 B2
(45) Date of Patent: *Jul. 11, 2023

(54) METHODS AND SYSTEMS FOR MANIFESTATION AND TRANSMISSION OF FOLLOW-UP NOTIFICATIONS

(71) Applicant: 3M INNOVATIVE PROPERTIES COMPANY, St. Paul, MN (US)

(72) Inventor: Gilan El Saadawi, Pittsburgh, PA (US)

(73) Assignee: 3M Innovative Properties Company, St. Paul, MN (US)

(*) Notice: Subject to any disclaimer, the term of this patent is extended or adjusted under 35 U.S.C. 154(b) by 98 days.

This patent is subject to a terminal disclaimer.

(21) Appl. No.: 17/303,663

(22) Filed: Jun. 4, 2021

(65) Prior Publication Data
US 2021/0296010 A1    Sep. 23, 2021

Related U.S. Application Data

(63) Continuation of application No. 15/872,532, filed on Jan. 16, 2018, now Pat. No. 11,043,306.
(Continued)

(51) Int. Cl.
*G16H 10/60* (2018.01)
*G16H 80/00* (2018.01)
(Continued)

(52) U.S. Cl.
CPC ............ *G16H 80/00* (2018.01); *G06F 16/93* (2019.01); *G06F 40/40* (2020.01); *G06Q 10/06* (2013.01);
(Continued)

(58) Field of Classification Search
CPC ........ G16H 10/60; G16H 80/00; G16H 50/70; G06F 40/295; G06F 40/237;
(Continued)

(56) References Cited

U.S. PATENT DOCUMENTS 5,065,315 A    11/1991  Garcia
5,148,366 A    9/1992   Buchanan
(Continued)

FOREIGN PATENT DOCUMENTS

EP    1361522    11/2003
EP    2030196    3/2009
(Continued)

OTHER PUBLICATIONS

Adam E.J. et al., "ESR guidelines for the communication of urgent and unexpected findings" European Society of Radiology (ESR), 2011, vol. 3, Issue (1), pp. 1-3.
(Continued)

*Primary Examiner* — Chris Parry
*Assistant Examiner* — Hassan A Khan

(57) ABSTRACT

A method for manifestation and transmission of follow-up notifications includes determining whether a document indicates a follow-up action associated with content in the document. The method includes generating at least one alert including an indication of the follow-up action. The method includes manifesting the at least one alert to at least one user.

20 Claims, 9 Drawing Sheets

Related U.S. Application Data

(60) Provisional application No. 62/446,897, filed on Jan. 17, 2017.

(51) Int. Cl.

| | | |
|---|---|---|
| *H04L 67/10* | (2022.01) | |
| *G06F 16/93* | (2019.01) | |
| *G06Q 10/06* | (2023.01) | |
| *G16H 50/70* | (2018.01) | |
| *G06F 40/40* | (2020.01) | |
| *G10L 15/26* | (2006.01) | |
| *G06N 20/00* | (2019.01) | |
| *G06N 5/04* | (2023.01) | |

(52) U.S. Cl.
CPC ............. *G16H 10/60* (2018.01); *G16H 50/70* (2018.01); *H04L 67/10* (2013.01); *G06N 5/04* (2013.01); *G06N 20/00* (2019.01); *G10L 15/26* (2013.01)

(58) Field of Classification Search
CPC ........ G06F 40/232; G06F 16/93; G06F 40/40; G06Q 10/06; H04L 67/10; G06N 20/00; G06N 5/04; G10L 15/26
See application file for complete search history.

(56) References Cited

U.S. PATENT DOCUMENTS

| | | | |
|---|---|---|---|
| 5,483,443 A | 1/1996 | Milstein | |
| 5,664,109 A * | 9/1997 | Johnson | G16H 10/60 706/45 |
| 5,823,948 A | 10/1998 | Ross, Jr. | |
| 6,006,183 A | 12/1999 | Lai | |
| 6,345,249 B1 | 2/2002 | Ortega | |
| 6,377,922 B2 | 4/2002 | Brown | |
| 6,529,876 B1 | 3/2003 | Dart | |
| 6,738,784 B1 | 5/2004 | Howes | |
| 6,834,264 B2 | 12/2004 | Lucas | |
| 7,236,968 B2 | 6/2007 | Seki | |
| 7,313,515 B2 | 12/2007 | Crouch | |
| 7,379,946 B2 | 5/2008 | Carus | |
| 7,447,988 B2 | 11/2008 | Ross | |
| 7,519,529 B1 | 4/2009 | Horvitz | |
| 7,584,103 B2 | 9/2009 | Fritsch | |
| 7,613,610 B1 | 11/2009 | Zimmerman | |
| 7,650,628 B2 | 1/2010 | Zimmerman | |
| 7,693,727 B2 | 4/2010 | Moore | |
| 7,716,040 B2 | 5/2010 | Koll | |
| 7,869,998 B1 | 1/2011 | Di | |
| 7,885,811 B2 | 2/2011 | Zimmerman | |
| 8,024,196 B1 | 9/2011 | Wodtke | |
| 8,050,938 B1 | 11/2011 | Green, Jr. | |
| 8,311,854 B1 | 11/2012 | Stanley | |
| 8,452,609 B2 | 5/2013 | Berg | |
| 8,463,673 B2 | 6/2013 | Koll | |
| 8,468,167 B2 | 6/2013 | Sathyanarayana | |
| 8,583,439 B1 | 11/2013 | Kondziela | |
| 8,706,521 B2 | 4/2014 | Ramarajan | |
| 8,781,829 B2 | 7/2014 | Koll | |
| 8,781,853 B2 | 7/2014 | Green | |
| 8,805,703 B2 | 8/2014 | Martin | |
| 8,862,483 B2 | 10/2014 | Scarola | |
| 9,082,310 B2 | 7/2015 | Koll | |
| 9,275,643 B2 | 3/2016 | Koll | |
| 9,424,523 B2 | 8/2016 | Koll | |
| 9,679,077 B2 | 6/2017 | Jagannathan | |
| 9,704,099 B2 | 7/2017 | Koll | |
| 9,996,510 B2 | 6/2018 | Koll | |
| 10,156,956 B2 | 12/2018 | Koll | |
| 10,325,296 B2 | 6/2019 | Koll | |
| 10,877,620 B2 | 12/2020 | Koll | |
| 11,043,306 B2 | 6/2021 | El Saadawi | |
| 2001/0042080 A1 | 11/2001 | Ross | |
| 2002/0029161 A1 * | 3/2002 | Brodersen | G06Q 10/1093 705/7.14 |
| 2002/0065854 A1 | 5/2002 | Pressly | |
| 2002/0077819 A1 | 6/2002 | Girardo | |
| 2002/0099717 A1 | 7/2002 | Bennett | |
| 2002/0120466 A1 | 8/2002 | Finn | |
| 2002/0198741 A1 | 12/2002 | Randazzo | |
| 2003/0074248 A1 | 4/2003 | Braud | |
| 2003/0105638 A1 | 6/2003 | Taira | |
| 2003/0133156 A1 | 7/2003 | Cragun | |
| 2003/0154085 A1 | 8/2003 | Kelley | |
| 2003/0229614 A1 | 12/2003 | Kotler | |
| 2004/0044546 A1 | 3/2004 | Moore | |
| 2004/0078215 A1 | 4/2004 | Dahlin | |
| 2004/0128163 A1 | 7/2004 | Goodman | |
| 2004/0240720 A1 | 12/2004 | Brantley | |
| 2004/0243545 A1 | 12/2004 | Boone | |
| 2005/0071194 A1 | 3/2005 | Bormann | |
| 2005/0102140 A1 | 5/2005 | Davne | |
| 2005/0137910 A1 | 6/2005 | Rao | |
| 2005/0158767 A1 | 7/2005 | Haskell | |
| 2005/0171819 A1 | 8/2005 | Keaton | |
| 2005/0203775 A1 * | 9/2005 | Chesbrough | G16H 80/00 705/2 |
| 2005/0228815 A1 | 10/2005 | Carus | |
| 2005/0273360 A1 | 12/2005 | Drucker | |
| 2006/0020492 A1 | 1/2006 | Cousineau | |
| 2006/0020493 A1 * | 1/2006 | Cousineau | G10L 15/1822 705/2 |
| 2006/0020886 A1 | 1/2006 | Agrawal | |
| 2006/0031194 A1 | 2/2006 | Ghazaleh | |
| 2006/0036472 A1 * | 2/2006 | Crockett | G16H 50/20 705/3 |
| 2006/0041428 A1 * | 2/2006 | Fritsch | G10L 15/1815 704/E15.024 |
| 2006/0047539 A1 | 3/2006 | Huang | |
| 2006/0089857 A1 * | 4/2006 | Zimmerman | G16Z 99/00 705/2 |
| 2006/0122865 A1 * | 6/2006 | Preiss | G16H 40/20 705/2 |
| 2006/0129435 A1 | 6/2006 | Smitherman | |
| 2006/0184393 A1 | 8/2006 | Ewin | |
| 2006/0277073 A1 | 12/2006 | Heilbrunn | |
| 2006/0282302 A1 * | 12/2006 | Hussain | G06Q 10/06 705/2 |
| 2007/0013968 A1 | 1/2007 | Ebaugh | |
| 2007/0016450 A1 | 1/2007 | Bhora | |
| 2007/0016451 A1 | 1/2007 | Tilson | |
| 2007/0027778 A1 | 2/2007 | Schellhammer | |
| 2007/0033073 A1 | 2/2007 | Tajaliawal | |
| 2007/0050187 A1 | 3/2007 | Cox | |
| 2007/0067185 A1 * | 3/2007 | Halsted | G16H 40/63 705/2 |
| 2007/0106751 A1 | 5/2007 | Moore | |
| 2007/0112599 A1 | 5/2007 | Liu | |
| 2007/0118410 A1 | 5/2007 | Nadai | |
| 2007/0143141 A1 | 6/2007 | Villasenor | |
| 2007/0143164 A1 | 6/2007 | Kaila | |
| 2007/0192143 A1 * | 8/2007 | Krishnan | G16H 10/20 600/300 |
| 2007/0198907 A1 | 8/2007 | Degala | |
| 2007/0203708 A1 | 8/2007 | Polcyn | |
| 2007/0226211 A1 | 9/2007 | Heinze | |
| 2007/0239499 A1 | 10/2007 | Shukla | |
| 2007/0276649 A1 | 11/2007 | Schubert | |
| 2007/0299651 A1 * | 12/2007 | Koll | G16H 10/60 704/235 |
| 2007/0299665 A1 * | 12/2007 | Koll | G16H 15/00 704/235 |
| 2008/0004505 A1 | 1/2008 | Pit | |
| 2008/0016164 A1 | 1/2008 | Chandra | |
| 2008/0028300 A1 | 1/2008 | Krieger | |
| 2008/0077451 A1 | 3/2008 | Anthony | |
| 2008/0141117 A1 | 6/2008 | King | |
| 2008/0147453 A1 | 6/2008 | Kogan | |
| 2008/0249374 A1 * | 10/2008 | Morita | G16H 15/00 600/300 |

(56) References Cited

U.S. PATENT DOCUMENTS

| | | | |
|---|---|---|---|
| 2009/0048833 A1* | 2/2009 | Fritsch | G10L 15/1815 704/235 |
| 2009/0070290 A1 | 3/2009 | Nye | |
| 2009/0077658 A1 | 3/2009 | King | |
| 2009/0089092 A1 | 4/2009 | Johnson | |
| 2009/0187407 A1* | 7/2009 | Soble | G10L 15/26 704/E13.011 |
| 2009/0192800 A1 | 7/2009 | Brandt | |
| 2009/0192822 A1 | 7/2009 | Regulapati | |
| 2009/0228299 A1 | 9/2009 | Kangarloo | |
| 2009/0271218 A1* | 10/2009 | Mok | G16H 70/20 705/2 |
| 2009/0287678 A1 | 11/2009 | Brown | |
| 2010/0076761 A1 | 3/2010 | Fritsch | |
| 2010/0099974 A1* | 4/2010 | Desai | G16H 15/00 707/708 |
| 2010/0100570 A1 | 4/2010 | Constantin | |
| 2010/0125450 A1* | 5/2010 | Michaelangelo | G06F 40/232 704/235 |
| 2010/0138241 A1* | 6/2010 | Ruark | G06Q 10/10 705/3 |
| 2010/0145720 A1* | 6/2010 | Reiner | G16Z 99/00 705/2 |
| 2010/0250236 A1* | 9/2010 | Jagannathan | G10L 15/1822 704/251 |
| 2010/0278453 A1 | 11/2010 | King | |
| 2010/0299135 A1 | 11/2010 | Fritsch | |
| 2010/0299320 A1 | 11/2010 | Claud | |
| 2010/0305997 A1 | 12/2010 | Ananian | |
| 2011/0043652 A1 | 2/2011 | King | |
| 2011/0055688 A1 | 3/2011 | Isidore | |
| 2011/0166875 A1 | 7/2011 | Hayter | |
| 2011/0239146 A1 | 9/2011 | Dutta | |
| 2011/0258001 A1* | 10/2011 | Green, III | G16H 40/20 705/3 |
| 2011/0295864 A1 | 12/2011 | Betz | |
| 2011/0301978 A1 | 12/2011 | Shiu | |
| 2012/0010900 A1 | 1/2012 | Kaniadakis | |
| 2012/0016690 A1* | 1/2012 | Ramarajan | G16H 50/20 705/2 |
| 2012/0041950 A1 | 2/2012 | Koll | |
| 2012/0065987 A1* | 3/2012 | Farooq | G16H 50/70 705/2 |
| 2012/0166220 A1 | 6/2012 | Baldwin | |
| 2012/0173255 A1 | 7/2012 | Korhnak | |
| 2012/0185275 A1 | 7/2012 | Loghmani | |
| 2012/0215551 A1 | 8/2012 | Flanagan | |
| 2012/0215782 A1* | 8/2012 | Jagannathan | G16H 10/60 707/740 |
| 2012/0239429 A1 | 9/2012 | Corfield | |
| 2012/0303365 A1 | 11/2012 | Finke | |
| 2012/0323572 A1 | 12/2012 | Koll | |
| 2012/0323598 A1* | 12/2012 | Koll | G16H 10/60 705/2 |
| 2013/0110547 A1 | 5/2013 | Englund | |
| 2013/0159408 A1* | 6/2013 | Winn | G06N 20/00 709/204 |
| 2013/0226617 A1 | 8/2013 | Mok | |
| 2013/0238330 A1 | 9/2013 | Casella | |
| 2014/0006431 A1 | 1/2014 | Jagannathan | |
| 2014/0047375 A1* | 2/2014 | Koll | G06F 40/174 715/780 |
| 2014/0052463 A1* | 2/2014 | Cashman | G06Q 10/1095 705/2 |
| 2014/0108047 A1 | 4/2014 | Kinney | |
| 2014/0164197 A1 | 6/2014 | Koll | |
| 2014/0278553 A1 | 9/2014 | Fritsch | |
| 2014/0288970 A1* | 9/2014 | Lee | G16H 30/40 705/2 |
| 2014/0324423 A1* | 10/2014 | Koll | G06F 40/166 704/235 |
| 2014/0343963 A1 | 11/2014 | Fritsch | |
| 2015/0066537 A1 | 3/2015 | Sheffer | |
| 2015/0088504 A1 | 3/2015 | Jagannathan | |
| 2015/0134349 A1 | 5/2015 | Vdovjak | |
| 2015/0278449 A1 | 10/2015 | Laborde | |
| 2015/0310362 A1 | 10/2015 | Huffman | |
| 2015/0356198 A1 | 12/2015 | D'Souza | |
| 2015/0356647 A1 | 12/2015 | Reiser | |
| 2015/0371145 A1 | 12/2015 | Koll | |
| 2016/0093010 A1 | 3/2016 | Vasiliu-Feltes | |
| 2016/0147955 A1 | 5/2016 | Shah | |
| 2016/0179770 A1 | 6/2016 | Koll | |
| 2016/0267232 A1 | 9/2016 | Koll | |
| 2016/0292392 A1* | 10/2016 | Xu | G16H 40/20 |
| 2016/0294964 A1* | 10/2016 | Brune | G06Q 10/109 |
| 2016/0335554 A1 | 11/2016 | Koll | |
| 2016/0371447 A1 | 12/2016 | Koman | |
| 2017/0068781 A1 | 3/2017 | Zasowski | |
| 2017/0109473 A1* | 4/2017 | Kulon | G16Z 99/00 |
| 2017/0270626 A1 | 9/2017 | Koll | |
| 2018/0040087 A1 | 2/2018 | Koll | |
| 2018/0081859 A1 | 3/2018 | Snider | |
| 2018/0101879 A1 | 4/2018 | Koll | |
| 2018/0276188 A1 | 9/2018 | Koll | |
| 2019/0026436 A1 | 1/2019 | Bender | |
| 2019/0065008 A1* | 2/2019 | Koll | G06F 3/0481 |

FOREIGN PATENT DOCUMENTS

| | | |
|---|---|---|
| EP | 2883203 | 6/2015 |
| EP | 3571608 | 11/2019 |
| JP | H09-106428 | 4/1997 |
| JP | 2005-267358 | 9/2005 |
| JP | 2006-509295 | 3/2006 |
| JP | 4037250 | 1/2008 |
| JP | 2008-108021 | 5/2008 |
| JP | 2009-211157 | 9/2009 |
| JP | 2011-118538 | 6/2011 |
| JP | 6339566 | 6/2018 |
| JP | 6388864 | 9/2018 |
| WO | WO 2005-122002 | 12/2005 |
| WO | WO 2009-143395 | 11/2009 |
| WO | WO 2011-100474 | 8/2011 |
| WO | WO 2012-048306 | 4/2012 |
| WO | WO 2012-177611 | 12/2012 |
| WO | WO 2015-079354 | 6/2015 |
| WO | WO 2015-136404 | 9/2015 |
| WO | WO 2018-136417 | 7/2018 |
| WO | WO 2019-103930 | 5/2019 |

OTHER PUBLICATIONS

Advisory Action dated Nov. 21, 2018 in U.S. Appl. No. 14/941,445 of Detlef Koll, filed Nov. 13, 2015, 2 pages.

Anonymous: "DMXzone Universal Form Validator PHP", Sep. 2, 2009, XP055432714, [online: https://www.dmxzone.com/Downloads/Tutorial_FormValidatorPHP_update_zip/FormValidatorPHP_update.pdf].

Anonymous: "Medical transcription—Wikipedia", Feb. 13, 2010, XP055465109, Retrieved from the Internet: URL: https://en.wikipedia.org/w/index.php?title=Medical_transcription&oldid=343657066 [Retrieved on Apr. 6, 2018].

Arup 106428 et al., "Context-based Speech Recognition Error Detection and Correction," Proceedings of HLT-NAACL 2004: Short Papers, May 2004, 4 pages.

Centers for Medicare & Medicaid Services, "Medicare Physician Guide: 1995 Documentation Guidelines for Evaluation and Management Services," 1995, 16 pages [online: https://www.cms.gov/Outreach-and-Education/Medicare-Learning-Network-MLN/MLNEdWebGuide/Downloads/95Docguidelines.pdf].

Centers for Medicare & Medicaid Services, "Medicare Physician Guide: 1997 Documentation Guidelines for Evaluation and Management Services," 1997, 49 pages [online: https://www.cms.gov/Outreach-and-Education/Medicare-Learning-Network-MLN/MLNEdWebGuide/Downloads/97Docguidelines.pdf].

Communication pursuant to Article 94(3) EPC dated Jan. 8, 2019 by the European Patent Office in patent application No. 13809956.9, 5 pages.

(56) References Cited

OTHER PUBLICATIONS

Communication Pursuant to Article 94(3) EPC, dated Jun. 27, 2019, in EPO application No. 14762803.6, 11 pages.
Daugherty B. et al., "Tracking Incidental Findings", Radiology Today, Jul. 2014, vol. 15, No. 7, p. 6.
Decision to Refuse European Application dated Oct. 24, 2019 in European Patent Application No. 11748231.5, 19 pages.
Dimick, Chris, "Quality Check: An Overview of Quality Measures and Their Uses," Journal of AHIMA 81, No. 9 (Sep. 2010); 34-38, Retrieved on May 14, 2013 from http://library.ahima.org/xpedio/groups/public/documents/ahima/bok1 _047952.hcsp?DocName= bok1_047952.
Examination Report dated Feb. 4, 2020, in Canadian patent application No. 2,904,656, 5 pages.
Examination Report dated Jun. 18, 2019, in Canadian patent application No. 2,811,942, 6 pages.
Examination Report received in Canadian patent application No. 2,791,292 dated Aug. 2, 2019, 7 pages.
Examination Report received in Canadian patent application No. 2,791,292 dated Mar. 9, 2020, 3 pages.
Examination Report received in Canadian patent application No. 2,791,292 dated Sep. 19, 2018, 9 pages.
Examiner's Report dated Apr. 15, 2019 in Canadian patent application No. 2,875,584, 4 pages.
Examiner's Report dated Dec. 20, 2018 in Canadian patent application No. 2,839,266, 4 pages.
Examiner's Report dated Jun. 27, 2019 in Canadian Patent Application No. 2,881,564, 6 pages.
Examiner's Report dated Nov. 29, 2019 in Canadian patent application No. 2,839,266, 4 pages.
Exhibit 1003 of Petition for Inter Parties Review of U.S. Pat. No. 8,781,829 filed before the Patent Trial and Appeal Board dated Dec. 21, 2018 by Petitioner Nuance Communications, Inc., Declaration of Andrew Sears.
Exhibit 1004 of Petition for Inter Parties Review of U.S. Pat. No. 8,781,829 filed before the Patent Trial and Appeal Board dated Dec. 21, 2018 by Petitioner Nuance Communications, Inc., Curriculum Vitae of Andrew Sears.
Exhibit 1005 of Petition for Inter Parties Review of U.S. Pat. No. 8,781,829 filed before the Patent Trial and Appeal Board dated Dec. 21, 2018 by Petitioner MModal Services Ltd., Michael Freeman Bliss, "Speech Recognition for Health Professionals", Pearson Prentice Hall, pp. 18-24, (2005).
Exhibit 1007 of Petition for Inter Parties Review of U.S. Pat. No. 8,781,829 filed before the Patent Trial and Appeal Board dated Dec. 21, 2018 by Petitioner Nuance Communications, Inc., Panzarasa et al., "Technical Solutions for Integrating Clinical Practice Guidelines with Electronic Patient Records", pp. 141-154, (2010).
Exhibit 1009 of Petition for Inter Parties Review of U.S. Pat. No. 8,781,829 filed before the Patent Trial and Appeal Board on Dec. 21, 2018 by Petitioner Nuance Communications, Inc., Joel D. Miller and Elizabeth M. Wenzel, "Recent Developments in SLAB: A Software-Based System for Interactive Spatial Sound Synthesis", Proceedings of 2002, Int'l Conf, on Auditory Display, pp. IDAC02 1-6, Jul. 2-5, 2002.
Exhibit 1010 of Petition for Inter Parties Review of U.S. Pat. No. 8,781,829 filed before the Patent Trial and Appeal Board dated Dec. 21, 2018 by Petitioner MModal Services Ltd., JCAHO—Specification Manual for National Implementation of Hospital Core Measures, Version 2.0 (Mar. 1, 2004).
Exhibit 1011 of Petition for Inter Parties Review of U.S. Pat. No. 8,781,829 filed before the Patent Trial and Appeal Board dated Dec. 21, 2018 by Petitioner MModal Services Ltd., JCAHO—Introduction and Background.
Exhibit 1012 of Petition for Inter Parties Review of U.S. Pat. No. 8,781,829 filed before the Patent Trial and Appeal Board dated Dec. 21, 2018 by Petitioner Nuance Communications, Inc., JCAHO—Using the Specifications Manual for National Implementation of Hospital Core Measures.

Exhibit 1013 of Petition for Inter Parties Review of U.S. Pat. No. 8,412,524 filed before the Patent Trial and Appeal Board dated Dec. 21, 2018 by Petitioner Nuance Communications, Inc., W. H. Auden, "Menu Selection and Form Filling", Semantic Organization, Chapter 3, 1970.
Exhibit 1014 of Petition for Inter Parties Review of U.S. Pat. No. 8,781,829 filed before the Patent Trial and Appeal Board dated Dec. 21, 2018 by Petitioner MModal Services Ltd., Alan J. Dix et al., "Human-Computer Interaction", 2nd ed., pp. 130-137, (1998).
Exhibit 1015 of Petition for Inter Parties Review of U.S. Pat. No. 8,781,829 filed before the Patent Trial and Appeal Board dated Dec. 21, 2018 by Petitioner Nuance Communications, Inc., Frequently Asked Questions: Signature Requirements, Cahaba Government Benefit Administrators (Mar. 2011).
Exhibit 1016 of Petition for Inter Parties Review of U.S. Pat. No. 8,781,829 filed before the Patent Trial and Appeal Board dated Dec. 21, 2018 by Petitioner Nuance Communications, Inc., WayBackMachine capture of CDC Website ICD-9-CM classification explanation, available at https://web.archive.org/web/20110430031819/https://www.cdc.gov/nchs/icd/icd9cm.htm (Apr. 30, 2011).
Exhibit 1017 of Petition for Inter Parties Review of U.S. Pat. No. 8,781,829 filed before the Patent Trial and Appeal Board dated Dec. 21, 2018 by Petitioner MModal Services Ltd., MModal's Preliminary Claim Construction Disclosure, *MModal Services Ltd* v. *Nuance Communications, Inc.*, Case No. 1:18-cv-00901-WMR (N.D. Ga. Dec. 3, 2018).
Exhibit 1018 of Petition for Inter Parties Review of U.S. Pat. No. 8,781,829 filed before the Patent Trial and Appeal Board dated Dec. 21, 2018 by Petitioner Nuance Communications, Inc., JCAHO Facts, Joint Commission on Accreditation of Healthcare Organizations, (Aug. 1, 2005).
Exhibit 1019 of Petition for Inter Parties Review of U.S. Pat. No. 8,781,829 filed before the Patent Trial and Appeal Board dated Dec. 21, 2018 by Petitioner Nuance Communications, Inc., Roe, D. B., & Wilpon, J. G. (Eds.). Voice communication between humans and machines. National Academies Press., pp. 165-198 (1994).
Exhibit 1020 of Petition for Inter Parties Review of U.S. Pat. No. 8,781,829 filed before the Patent Trial and Appeal Board dated Dec. 21, 2018 by Petitioner MModal Services Ltd., Win Phillips, "Introduction to Natural Language Processing, Consortium on Cognitive Science Instruction (Apr. 1999)", available at https://web.archive.org/web/20090221020728/http:/www.mind.lstu.edu/curriculum/protothinker/natural_language_processing.php (Sep. 1, 2006).
Exhibit 1021 of Petition for Inter Parties Review of U.S. Pat. No. 8,781,829 filed before the Patent Trial and Appeal Board dated Dec. 21, 2018 by Petitioner Nuance Communications, Inc., Laurence S. Gillick, "A Rapid Match Algorithm for Continuous Speech Recognition", HLT 1990 Proceedings of the Workshop on Speech and Natural Language, pp. 170-172, (Jun. 24, 1990).
Exhibit 1022 of Petition for Inter Parties Review of U.S. Pat. No. 8,781,829 filed before the Patent Trial and Appeal Board datd Dec. 21, 2018 by Petitioner Nuance Communications, Inc., Declaration of Dr. James Mullins regarding Public availability of Panzarasa, pp. 111-153.
Exhibit 1022 of Petition for Inter Parties Review of U.S. Pat. No. 8,781,829 filed before the Patent Trial and Appeal Board dated Dec. 21, 2018 by Petitioner MModal Services Ltd., Declaration of Dr. James Mullins regarding public availability of Panzarasa, pp. 244-273 end.
Exhibit 1022 of Petition for Inter Parties Review of U.S. Pat. No. 8,781,829 filed before the Patent Trial and Appeal Board dated Dec. 21, 2018 by Petitioner MModal Services Ltd., Declaration of Dr. James Mullins regarding public availability of Panzarasa, pp. 67-110.
Exhibit 1022 of Petition for Inter Parties Review of U.S. Pat. No. 8,781,829 filed before the Patent Trial and Appeal Board dated Dec. 21, 2018 by Petitioner Nuance Communications, Inc., Declaration of Dr. James Mullins regarding public availability of Panzarasa, pp. 154-201.
Exhibit 1022 of Petition for Inter Parties Review of U.S. Pat. No. 8,781,829 filed before the Patent Trial and Appeal Board dated Dec. 21, 2018 by Petitioner Nuance Communications, Inc., Declaration of Dr. James Mullins regarding Public availability of Panzarasa, pp. 1-66.

(56) References Cited

OTHER PUBLICATIONS

Exhibit 1022 of Petition for Inter Parties Review of U.S. Pat. No. 8,781,829 filed before the Patent Trial and Appeal Board dated Dec. 21, 2018 by Petitioner Nuance Communications, Inc., Declaration of Dr. James Mullins regarding public availability of Panzarasa, pp. 202-243.
Extended European Search Report dated Sep. 25, 2020, in European patent application No. 18741689.6, 14 pages.
Final Office Action dated Sep. 4, 2018 in U.S. Appl. No. 14/218,220 of Juergen Fritsch, filed Mar. 18, 2014, 46 pages.
Final Rejection dated Jan. 21, 2021 for U.S. Appl. No. 15/993,958 of Detlef Koll, filed May 31, 2018, 21 pages.
Final Rejection dated Jul. 14, 2020 for U.S. Appl. No. 15/788,522 of Detlef Koll, filed Oct. 19, 2017, 33 pages.
Final Rejection dated Mar. 16, 2020 for U.S. Appl. No. 15/993,958 of Detlef Koll, filed May 31, 2018, 33 pages.
Final Rejection dated Nov. 19, 2020 for U.S. Appl. No. 16/193,443 of Derek L. Nichols, filed Nov. 16, 2018, 42 pages.
Final Rejection dated Nov. 5, 2019 for U.S. Appl. No. 14/941,445 of Detlef Koll, filed Nov. 13, 2015, 19 pages.
Final Rejection dated Oct. 11, 2018 for U.S. Appl. No. 14/941,445 of Detlef Koll, filed Nov. 13, 2015, 16 pages.
Final Rejection dated Oct. 29, 2020 for U.S. Appl. No. 15/616,884 of Detlef Koll, filed Jun. 7, 2017, 9 pages.
First Examination Report dated Aug. 29, 2019 in Indian patent application No. 448/MUMNP/2013, 6 pages.
First Examination Report dated Dec. 24, 2019, in Indian patent application No. 336/DELNP/2014, 7 pages.
First Examination Report dated Oct. 7, 2019 in Indian patent application No. 7449/DELNP/2012, 9 pages.
First Examination Report in Indian patent application No. 2186/MUMNP/2012 dated Jul. 19, 2019, 7 pages.
Hassanpour Saeed et al., "Information extraction from multi-institutional radiology reports," Artificial Intelligence in Medicine, Elsevier NL, vol. 66, Oct. 3, 2015, pp. 29-39.
International Preliminary Report on Patentability, dated Aug. 1, 2019 in International Patent Application No. PCT/US2018/013868, 9 pages.
International Search Report and Written Opinion received for PCT Patent Application No. PCT/US2018/013868, dated Jun. 18, 2018, 14 pages.
International Search Report and Written Opinion received for PCT Patent Application No. PCT/US2018/061517, dated Mar. 7, 2019, 10 pages.
James Flanagan, et al. "Defining the Standards for Automated E&M Coding Through Coding Consistency Methodology," Perspectives in Health Information Management, CAC Proceedings; Fall 2008, 7 pages [online: http://perspectives.ahima.org/defining-the-standards-for-automated-earn-coding-through-coding-consistency-methodology/ ].
"Medical Decision Making and the Marshfield Clinic Scoring Tool FAQ," American College of Emergency Physicians, May 24, 2017, 3 pages, [online: https://www.acep.org/administration/reimbursement/reimbursement-faqs/medical-decision-making-and-the-marshfield-clinic-scoring-tool-faq/#sm.000019luk7uslud34somv72pq17x3].
Meliha Yetisgen-Yildiz et al., "A text processing pipeline to extract recommendations from radiology reports," Journal of Biomedical Informatics, vol. 46, No. 2, Jan. 24, 2013, pp. 354-362.

Non Final Rejection dated Apr. 6, 2020 for U.S. Appl. No. 15/616,884 of Detlef Koll, filed Jun. 7, 2017, 7 pages.
Non Final Rejection dated Jun. 10, 2020 for U.S. Appl. No. 15/993,958 of Detlef Koll, filed May 31, 2018, 14 pages.
Non Final Rejection dated Mar. 19, 2020 for U.S. Appl. No. 16/174,503 of Detlef Koll, filed Oct. 30, 2018, 43 pages.
Non Final Rejection dated May 14, 2020 for U.S. Appl. No. 16/193,443 of Derek L. Nichols, filed Nov. 16, 2018, 64 pages.
Non-Final Office Action dated Sep. 4, 2018 in U.S. Appl. No. 15/839,037 of Detlef Koll, filed Dec. 12, 2017, 22 pages.
Non-Final Rejection dated Jan. 9, 2020 for U.S. Appl. No. 15/788,522 of Detlef Koll, filed Oct. 19, 2017, 55 pages.
Non-Final Rejection dated Jul. 22, 2019 in U.S. Appl. No. 14/941,445 of Detlef Koll, filed Nov. 13, 2015, 29 pages.
Non-Final Rejection dated Mar. 6, 2020 in U.S. Appl. No. 14/941,445 of Detlef Koll, filed Nov. 13, 2015, 16 pages.
Non-Final Rejection dated Sep. 16, 2019 for U.S. Appl. No. 15/993,958 of Detlef Koll, filed May 31, 2018, 65 pages.
Notice from the European Patent Office dated Oct. 1, 2007 concerning business methods, Journal of the European Patent Office, XP007905525, vol. 30, No. 11, pp. 592-593 (Oct. 1, 2007).
Notice of Allowance dated Nov. 3, 2020 for U.S. Appl. No. 14/941,445 of Detlef Koll, filed Nov. 13, 2015, 42 pages.
Notice of Allowance dated Sep. 11, 2020 for U.S. Appl. No. 16/174,503 of Detlef Koll, filed Oct. 30, 2018, 33 pages.
OpenVpms, Follow-up tasks, Submitted by Matt C on Fri, Sep. 17, 2010, Available at: https://openvpms.org/project/followup-task-lists-enhancements.
Petition for Inter Parties Review of U.S. Pat. No. 8,781,829 filed before the Patent Trial and Appeal Board dated Dec. 21, 2018 by PetitionerNuance Communications, Inc., 81 pages.
Sayon Dutta et al., "Automated Detection Using Natural Language Processing of Radiologists Recommendations for Additional Imaging of Incidental Findings," Annals of Emergency Medicine, vol. 62, No. 2, Aug. 1, 2013, pp. 162-169.
Second Examiner's Report dated May 20, 2020, in Canadian patent application No. 2,875,584, 5 pages.
Slabodkin Greg, "CMS proposed rulereduces Evaluation andManagement coding burden",Jul. 13, 2018, 4 pages, "https://www.healthdatamanagement.com/news/cms-proposed-rule-reduces-evaluation-and-management-coding-burden?reconf=1".
Stephanie L. Jones "E/M Audit Tool: To be used with AAPC Specialty examinations," 2006 reprinted by American Academy of Professional Coders, 2 pages [online: https://c.ymcdn.com/sites/www.txosteo.org/resource/resmgr/imported/EM%20AuditTool%20from%20Practicum.pdf].
Summons to Attend Oral Proceedings Pursuant to Rule 115(1) EPC dated Jun. 12, 2019 in European Patent Application No. 11748231.5, 11 pages.
Summons to Attend Oral Proceedings Pursuant to Rule 115(1) EPC dated Mar. 24, 2020, by the European Patent Office in patent application No. 13809956.9, 10 pages.
Summons to Attend Oral Proceedings pursuant to Rule 115(1) EPC dated Oct. 31, 2018, in European Patent Application No. 12802338.9, 8 pages.
Yildiz M.Y. et al., "A text processing pipeline to extract recommendations from radiology reports", Journal of Biomedica Informatics, 2013, vol. 46, pp. 354-362.

\* cited by examiner

100 ⤵

COMPUTING DEVICE 101

VALUE SET 121

VALUE SET DEFINITION

⌄@mmodal.snomed.nodule.description
- INCLUDE BILOBAR (QUALIFER VALUE)
- INCLUDE CAVITARY (QUALIFER VALUE)
- INCLUDE CIRCUMSCRIBED (QUALIFER VALUE)
- INCLUDE COARSE (QUALIFER VALUE)
- INCLUDE COLD (QUALIFER VALUE)
- INCLUDE COMPLEX (QUALIFER VALUE)
- INCLUDE DISCRETE (QUALIFER VALUE)
- INCLUDE DOMINANT (QUALIFER VALUE)
- INCLUDE ENCAPSULATED (QUALIFER VALUE)
- INCLUDE INDISTINCT (QUALIFER VALUE)
- INCLUDE LOCULATED (QUALIFER VALUE) [AND DESCENDANTS]
- INCLUDE NON-SPECIFIC (QUALIFER VALUE)
- INCLUDE NON-TOXIC (QUALIFER VALUE)
- INCLUDE PEDUNCULATED (QUALIFER VALUE)
- INCLUDE PROMINENT (QUALIFER VALUE)
- INCLUDE SIMPLE (QUALIFER VALUE)
- INCLUDE SMOOTH (QUALIFER VALUE)
- INCLUDE SOFT (QUALIFER VALUE)
- INCLUDE SPONGIFORM (QUALIFER VALUE)
- INCLUDE TOXIC (QUALIFER VALUE)
- INCLUDE VAGUE (QUALIFER VALUE)

FIG. 1C

METHODS AND SYSTEMS FOR MANIFESTATION AND TRANSMISSION OF FOLLOW-UP NOTIFICATIONS

BACKGROUND

The disclosure relates to transmitting notifications. More particularly, the methods and systems described herein relate to transmitting notifications generated based upon follow-up recommendations within one or more analyzed documents.

Communication breakdown is reported to be a significant cause of malpractice lawsuits. Breakdowns in communication may occur between specialists (e.g., radiologists) and physicians referring patients to the specialists. For example, certain specialists are required to attempt to coordinate their efforts with those of the referring physician; however, this has the unintended consequence of the specialists spending large parts of their days attempting to contact referring physicians without necessarily improving a level of communication between the specialists and the referring physicians.

What is needed are improved techniques for generating, manifesting, and transmitting follow-up notifications.

BRIEF SUMMARY

In one aspect, a method for manifestation and transmission of follow-up notifications includes determining whether a document requires a follow-up action associated with content in the document. The method includes generating at least one alert including an indication of the follow-up action. The method includes manifesting the at least one alert to at least one user. In one embodiment, the method further includes automatically transmitting the at least one alert to the at least one user in an electronic message.

In another aspect, a non-transitory computer-readable medium tangibly stores computer program instructions executable by at least one computer processor to perform a method for manifestation and transmission of follow-up notifications, including determining whether a document requires a follow-up action associated with content in the document, generating at least one alert including an indication of the follow-up action, and manifesting the at least one alert to at least one user.

Other features and advantages of various aspects and embodiments of the present invention will become apparent from the following description and from the claims.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1C is a block diagram depicting one embodiment of a value set associated with an information model;

DETAILED DESCRIPTION

In one aspect, the methods and systems described herein provide a method for detecting indications of follow-up recommendations within documents (such as, without limitation, within radiology reports) and for manifesting at least one alert for automatic communication between a physician and a specialist (e.g., between a referring physician and a radiologist). In some embodiments, a workflow application generates automatic alerts and transmits the automatically generated alerts via email or text to at least one recipient providing reminders of follow-up action items.

Figure 1A:
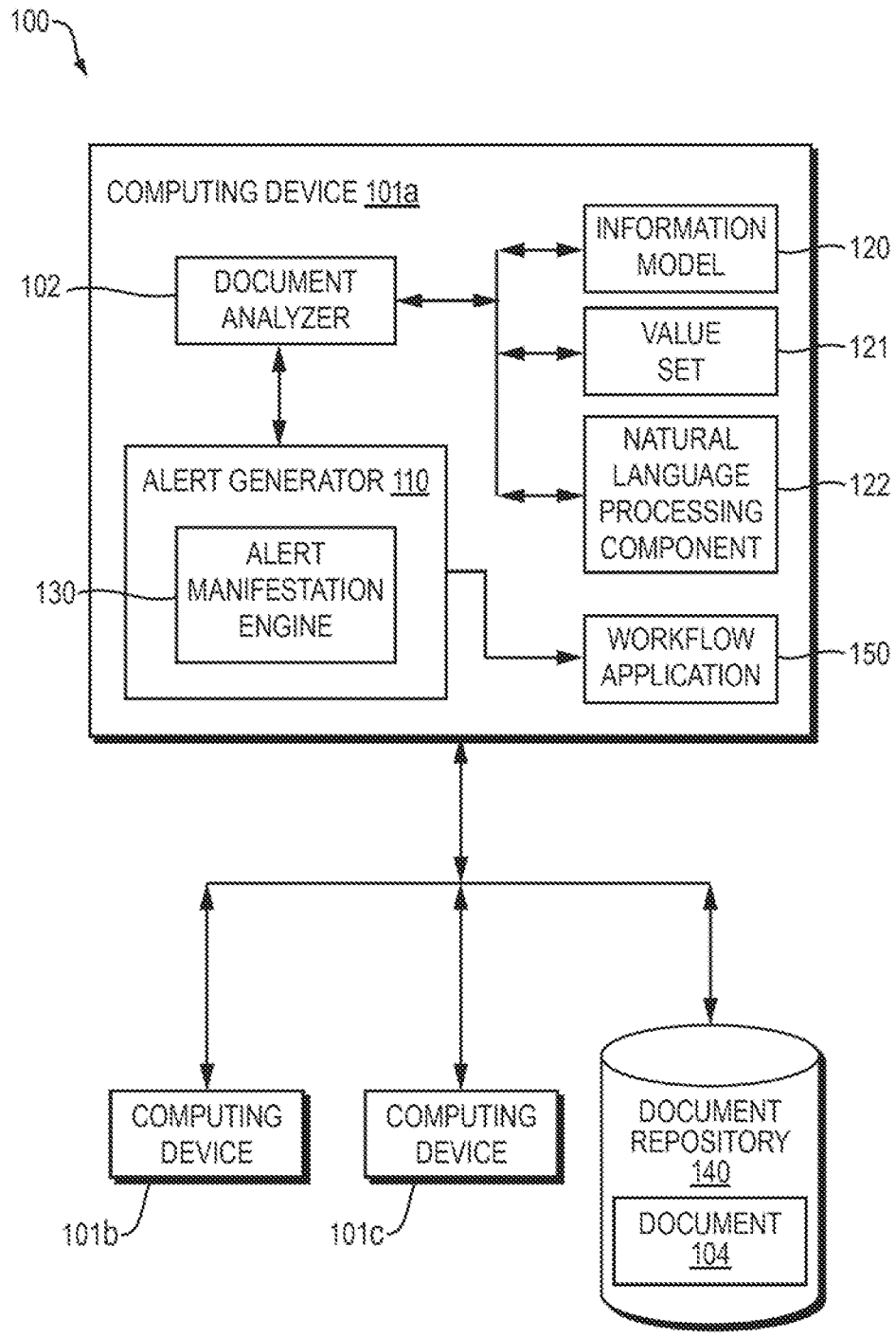
FIG. 1A is a block diagram depicting one embodiment of a system for generation of follow-up notifications.
Figure 1B:
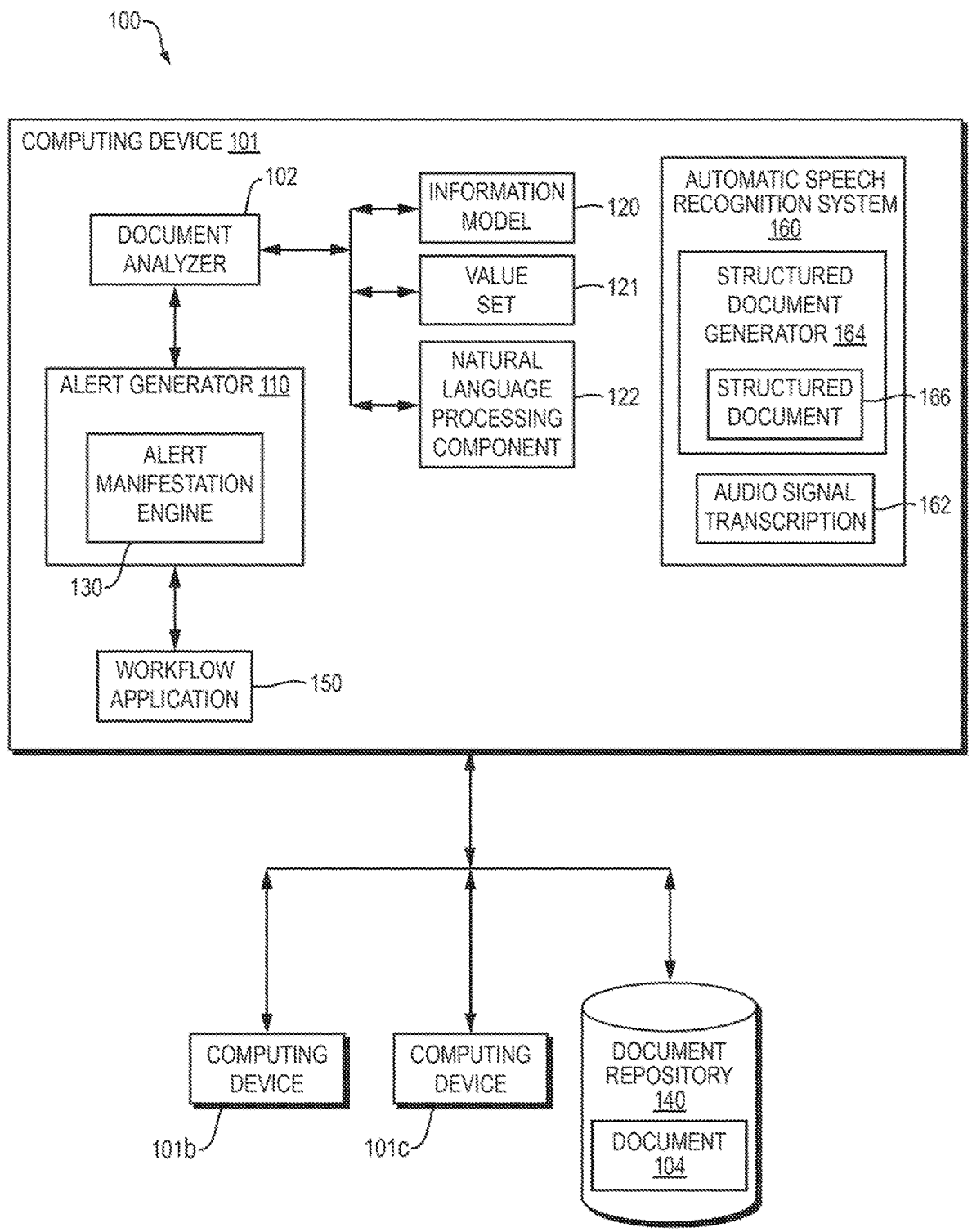
FIG. 1B is a block diagram depicting one embodiment of a system for generation of follow-up notifications including automatic speech recognition functionality.
Figure 2:
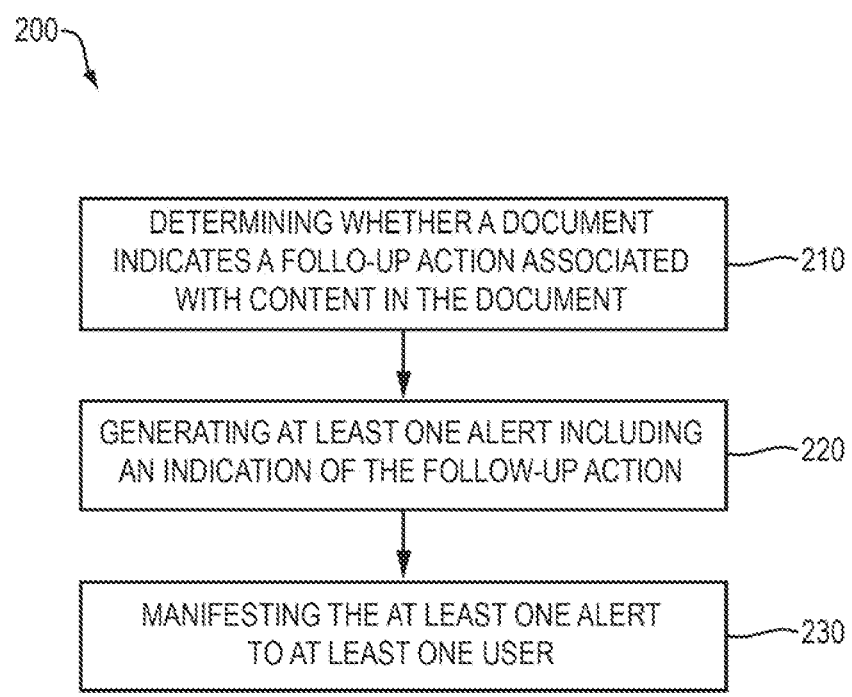
FIG. 2 is a flow diagram depicting one embodiment of a method for generation of follow-up notifications.

Referring now to FIGS. 1A and 1B, in conjunction with FIG. 2, in brief overview, the method 200 includes determining whether a document indicates a follow-up action associated with content in the document 210. The method 200 includes generating at least one alert including an indication of the follow-up action 220. The method 200 includes manifesting the at least one alert to at least one user 230. In some embodiments, the components described herein may execute one or more functions automatically, that is, without human intervention, in order to make the determination, the generation, and the manifestation. For example, the system 100 may receive access to one or more documents 104 and automatically proceed to execute the method 200 described below.

Referring now to FIG. 2 in further detail, the method 200 includes determining whether a document indicates a follow-up action associated with content in the document 210. A document analyzer 102 may automatically access a document 104 to determine whether the document 104 indicates a follow-up action associated with content in the document 104.

The document analyzer 102 may be provided as a software module. The document analyzer 102 may be provided as a hardware module. The computing device 101a may execute the document analyzer 102.

The document analyzer 102 may automatically retrieve the document 104 from a document repository 140. The document 104 may be any type of document, structured (e.g., without limitation, computer readable) and/or unstructured (e.g., free form text), generated by any source (e.g., a transcription of human speech), a form or report completed by a human (manually or via dictation or other means), a result of a medical procedure (such as, without limitation, an X-ray, or other document source). Examples of techniques that may be used to generate structured documents (such as, without limitation, eXtended Markup Language (XML) documents, documents that comply with the Fast Healthcare Interoperability Resources Specification, and documents that comply with standards provided by Health Level Seven International) may be found, for example, in commonly-owned U.S. Pat. No. 7,584,103, entitled, "Automated Extraction of Semantic Content and Generation of a Structured Document from Speech," which is hereby incorporated by reference herein; commonly-owned U.S. Pat. No. 7,716,040, entitled, "Verification of Extracted Data," which is hereby incorporated by reference herein; and the patents, patent applications, and other documents cited therein. The document 104 may include implicit and/or explicit recommendations for actions to be taken by at least one person—for example, by the speaker or by an intended audience of the speaker.

The document repository 140 may be a database of any type. Examples of a document repository 140 database include, without limitation, structured storage (e.g., NoSQL-type databases and BigTable databases), HBase databases distributed by The Apache Software Foundation of Forest Hill, Md., MongoDB databases distributed by 10Gen, Inc. of New York, N.Y., Cassandra databases distributed by The Apache Software Foundation, and document-based databases. In other embodiments, the document repository 140 is an ODBC-compliant database. For example, the document repository 140 may be provided as an ORACLE database manufactured by Oracle Corporation of Redwood City, Calif. In other embodiments, the document repository 140 may be a Microsoft ACCESS database or a Microsoft SQL server database manufactured by Microsoft Corporation of Redmond, Wash. In still other embodiments, the document repository 140 may be a custom-designed database based on an open source database, such as the MYSQL family of freely available database products distributed by Oracle Corporation.

The document analyzer 102 analyzes the document 104 to determine whether the document 104 indicates, explicitly or implicitly, a follow-up action associated with content in the document 104. In one embodiment, the document analyzer 102 uses an information model 120 as part of this analysis. An information model 120 may be a representation of concepts and their relationships, constraints, rules, and operations to specify data semantics for a chosen domain; the information model 120 may be used to share an organized view of the domain knowledge. When describing the data modeling of an information model 120, a formal representation of relationships and the operations that can be performed on sets of data may be used. When referring to specific instances of data, a value set 121 may be used for each of a plurality of types included in the information model 120. For example, to diagnose diabetes, an information model 120 of what would make up the diagnosis of diabetes may be generated including, for example, types, signs, symptoms, lab results, medications; then, the system 100 may create a value set 121 for each of those elements (e.g., types would equal either type 1 diabetes or type 2 diabetes, lab results may include a range of values that are indicative of diabetes).

In some embodiments, the document analyzer 102 communicates with, or provides the functionality of, a natural language processing component 122.

The natural language processing component 122 may be provided as a software module. The natural language processing component 122 may be provided as a hardware module. The computing device 101a may execute the natural language processing component 122. The natural language processing component 122 may execute on a separate computing device with which the computing device 101a is in communication (not shown). The document analyzer 102 may leverage the functionality of a natural language processing component 122 to identify information within the document 104 that may indicate a follow-up action. The document analyzer 102 may apply, by a natural language processing engine, a machine learning model to content in the document 104 to determine whether the content in the document 104 includes language associated with the follow-up action. The document analyzer 102 may apply, by a natural language processing engine, a machine learning model to content in the document 104 to determine whether the content in the document 104 includes language associated with a finding implicitly indicating the follow-up action. Alternatively, the document analyzer 102 may apply, by a natural language processing engine, a machine learning model to a document 104 to identify content within the document 104 that the document analyzer 102 can use in conjunction with the information model 120 to determine whether the content in the document 104 includes language associated with the follow-up action.

In some embodiments, the natural language processing component 122 extracts concepts and/or content from the document 104, the document analyzer 102 populates a value set 121 of the information model 120 with the extracted content, and the document analyzer 102 analyzes the populated information model 120 to determine whether the document 104 indicates a follow-up action associated with content in the document 104. Examples of techniques that may be used to extract concepts and/or content from the document 104 may be found, for example, in commonly-owned U.S. Pat. No. 7,584,103, entitled, "Automated Extraction of Semantic Content and Generation of a Structured Document from Speech"; commonly-owned U.S. Pat. No. 7,716,040, entitled, "Verification of Extracted Data"; and the patents, patent applications, and other documents cited therein.

In one embodiment, the document analyzer 102 determines whether a document 104 indicates a follow-up action by detecting one or more components of a follow-up action. Examples of such components include, without limitation, language expressing a follow-up action item, recommendations for particular procedures or visits, and dates or times of follow-up. The document analyzer 102 may apply an information model 120 to determine whether the document 104 indicates a follow-up action associated with content in the document 104. The document analyzer 102 may apply the information model 120 to determine whether the content in the document 104 includes language associated with the follow-up action. The document analyzer 102 may apply the information model 120 to determine whether the content in the document 104 includes an identification of a recommended procedure associated with the follow-up action. The document analyzer 102 may apply the information model 120 to determine whether the content in the document 104 includes an identification of a date associated with the follow-up action. The document analyzer 102 may apply the information model 120 to determine whether the content in the document 104 includes an identification of a time associated with the follow-up action.

The method 200 may include applying a rule to determine whether the content in the document 104 includes an identification of a recommended procedure associated with the follow-up action. In some embodiments, the document analyzer 102 determines that a document 104 explicitly indicates a follow-up action. By way of example, and without limitation, the document 104 may include text explicitly stating, "Consider ultrasound in 1 month for further evaluation, if clinically warranted." In such an example, the document analyzer 102 may identify "consider for further evaluation" as language expressive of a follow-up action item, the document analyzer 102 may identify "ultrasound" as an action needed, and the document analyzer 102 may identify "in 1 month" as dates or times on which follow-up occurred (or, in other embodiments in which the time and date have not yet passed, as a date or time on which to schedule a follow-up). The document analyzer 102 may make these identifications by applying rules from the information model 120.

In one embodiment, the method 200 includes generating the information model 120 and a value set 121 associated with the information model 120 to identify implicit follow-up recommendations. Implicit follow-up recommendations may include recommendations such as, for example, those recommendations based on national standards.

In some embodiments, the information model 120 includes data associated with content in the document 104. For example, the information model 120 may include an enumeration of sub-categories of a category of content in the document 104; for example, the information model 120 may include an identification of a category "diabetes" and include an identification of two sub-types of the "diabetes" category, "Type I" and "Type 2." The information model 120 may include an identification of at least one symptom associated with a category. The information model 120 may include data used to identify information about the content in a document 104, such as for generating a conclusion about the content based on an analysis of information in the information model 120.

In other embodiments, the information model 120 includes at least one rule. By way of example, a rule in the information model 120 may specify that if an identification of a medication treating diabetes is included in the document 104 and if an identification of at least one symptom is included in the document 104, the system should conclude that the patient has diabetes even if a statement to that effect has not been explicitly included in the document 104. In still other embodiments, instead of including the at last one rule, the information model 120 accesses at least one rule stored in a separate data structure than the information model 120.

In further embodiments, the information model 120 is a representation of concepts and their relationships, constraints, rules, and operations to specify data semantics for a chosen domain; it allows the representation of a conceptual model to an implementable schema. In one of these embodiments, the information model 120 is constructed using medical knowledge in order to model the medical record data in diagnosing medical conditions using clinical picture of patient, lab results, radiology findings and treatment medication and procedures to view a more accurate overview of patient.

In one embodiment, value sets 121 associated with the information model 120 are created based on medical knowledge and national standards. As an example, and without limitation, implicit follow up recommendation of an incidental findings within a document 104 associated with radiology may be developed based on the American College of Radiologists (ACR) recommendations that represent the standard of care in patient management.

The document analyzer 102 may apply the information model 120 and the value set 121 to identify an implicit follow-up action. For example, the document analyzer 102 may identify a rule within the information model 120 to apply to make the determination. By way of example, the information model 120 may specify that if a particular value in the value set 121 is set to a certain value, a certain rule should be applied to identify a recommended procedure (e.g., if "type" is set to "Type 1 diabetes" in a diabetes-related information model 120, the information model 120 may specify a rule to be applied and the rule may identify a foot exam as a recommended procedure).

As another example, a document 104 may include text such as "follow-up can be obtained in 12 months" or "routine follow-up is recommended" without providing any additional specificity—the former example does not provide an explicit description of a procedure or other item to be followed up on; the latter example does not provide an explicit description of either a procedure or an indication as to when the routine follow up should occur. In such an example, the document analyzer 102 may analyze a type of study or other content included in the document 104 to identify a follow-up action.

Referring now to FIG. 1C, a block diagram depicts one embodiment of a value set 121 associated with an information model 120. As shown in FIG. 1C, a sample value set 121 enumerates a plurality of values that are associated with a nodule (e.g., whether the nodule is smooth or coarse, toxic or non-toxic, prominent or indistinct, et al.). The document analyzer may set values for a subset of those values based upon analyzing a content of document 104 and then use the subset of values to identify an associated rule within the information model 120.

Figure 1D:
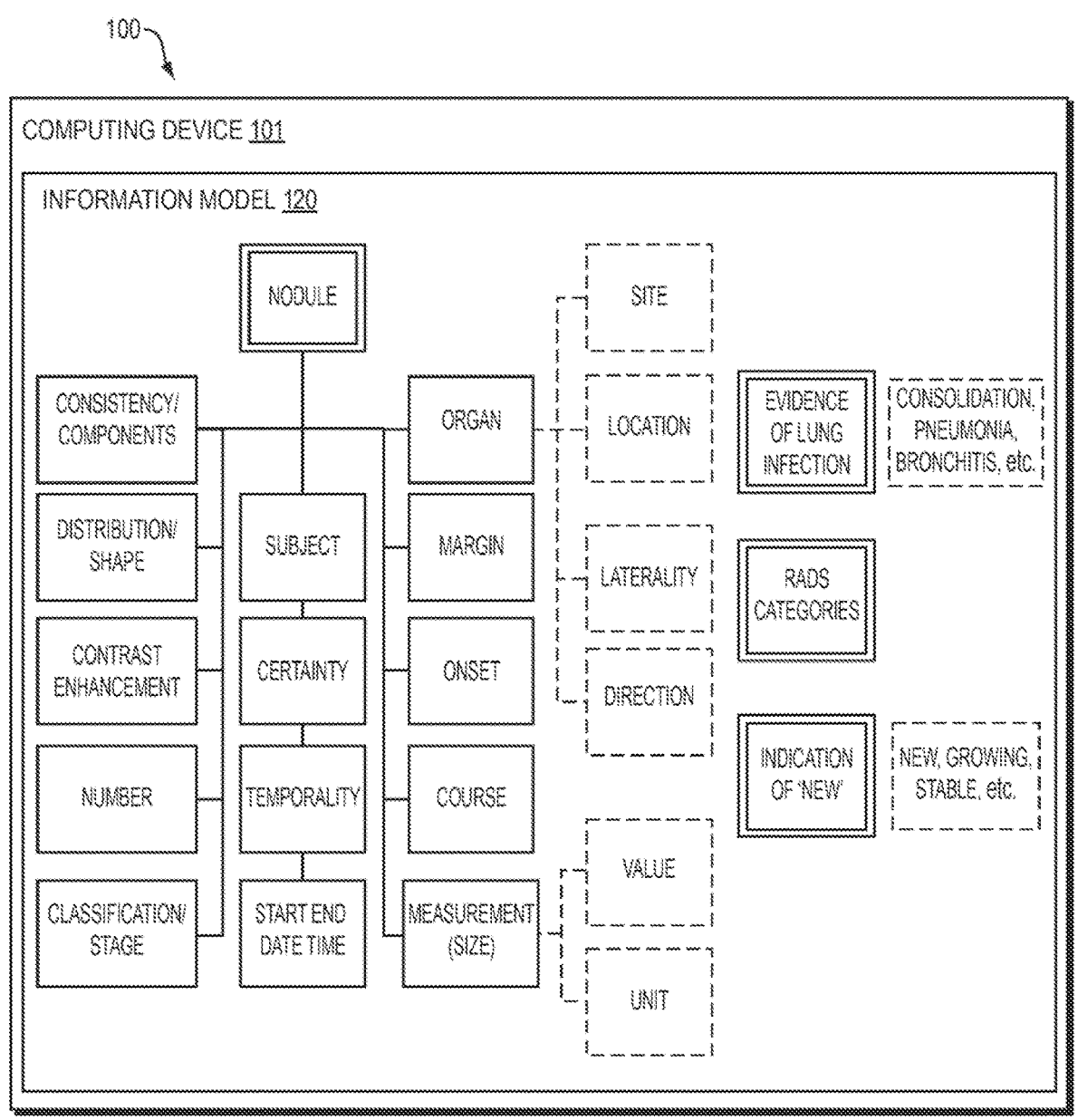
FIG. 1D is a block diagram depicting one embodiment of an information model 120.

Referring now to FIG. 1D, a block diagram depicts one embodiment of an information model 120. FIG. 1D depicts the types of information modeled in connection with content in the document 104; in the example shown in FIG. 1D, the information model 120 relates to a nodule and models information such as where the nodule is located (e.g., organ site and organ location), a number of nodules, consistency of the nodule, and measurements of the nodules. In one embodiment, the document analyzer 102 uses the information shown in FIG. 1D to make a determination regarding a follow-up action. In another embodiment, the document analyzer 102 uses the information shown in FIG. 1D as well as other information in the model 120 (not shown), such as particular rules for identifying follow-up actions, to make a determination regarding a follow-up action.

Figure 1E:
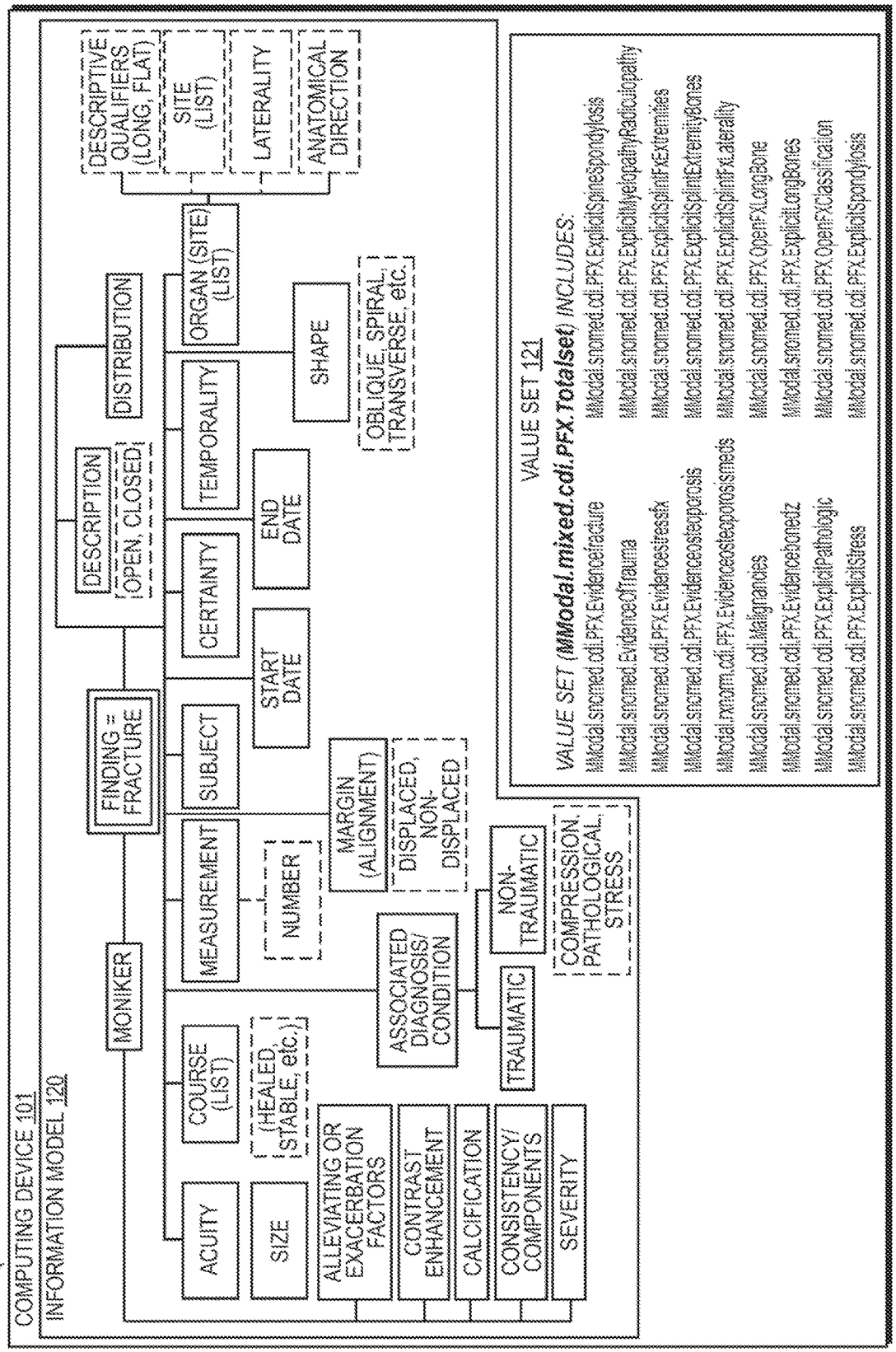
FIG. 1E is a block diagram depicting one embodiment of an information model 120 and an associated rule set 121.

Referring now to FIG. 1E, a block diagram depicts one embodiment of an information model 120 and an associated rule set 121. As shown in FIG. 1E, an information model 120 may include additional information such as relationships to evidence of trauma or diseases like malignancy, providing a more accurate diagnosis of cause of fracture.

Referring back to FIG. 2, the method 200 includes generating at least one alert including an indication of the follow-up action 220. In one embodiment, the system 100 may include functionality specially programmed to generate the alert, such as the alert generator 110. The alert generator 110 may be a software module. The alert generator 110 may be a hardware module. In another embodiment, a workflow application 150 may provide the functionality of the alert generator 110.

The alert generator 110 may include an alert manifestation engine 130. The alert generator 110 may be in communication with an alert manifestation engine 130. The alert manifestation engine 130 may be a software module. The alert manifestation engine 130 may be a hardware module. In another embodiment, a workflow application 150 may provide the functionality of the alert manifestation engine 130.

The alert generator 110 may receive an indication from the document analyzer 102 of an action indicated by the document 104. The alert generator 110 may receive an indication from the workflow application 150 of an action indicated by the document 104. The alert generator 110 may receive the identification of the at least one alert recipient from the workflow application 150. By way of example, the document analyzer 102 may transmit an indication to the alert generator 110 to generate an alert including an indication of the follow-up action; the alert generator 110 may transmit the indication of the follow-up action to the workflow application 150, which may provide the alert generator 110 with contact information for one or more users who should receive the alert(s).

The alert generator 110 may identify at least one alert recipient. The alert generator 110 may identify a single alert recipient to receive multiple alerts. For example, the alert generator 110 may generate a first alert for the physician to schedule an ultrasound for the patient and generate a second alert for the physician to follow up with the patient regarding the recommendation to have an ultrasound done. The alert generator 110 may identify multiple alert recipients to receive the same alert. The alert generator 110 may identify multiple alert recipients to receive different alerts. The alert generator 110 may generate one alert from the document 104. The alert generator 110 may generate multiple alerts from a single document 104. For example, the alert generator 110 may generate a first alert for a physician and a second alert for a patient, based on the same radiology report document 104. The alert generator 110 executing on the computing device 101a may generate one or more alerts automatically and without human intervention.

The alert generator 110 may generate at least one alert including a date on which to take the indicated follow-up action. The alert generator 110 may receive the date from the document analyzer 102; the document analyzer 102 may provide the alert generator 110 with the date identified by the information model 120. The alert generator 110 may access the information model 120 directly, querying the information model 120 and retrieving the date. The alert generator 110 may receive the date from the workflow application 150.

As will be understood by one of ordinary skill, the indication of the follow-up action in the generated alert may take a different form than the indication of the follow-up action within the document 104. By way of example, the indication of the follow-up action may be implied by the content of the document 104 (e.g., content of the document 104 may be associated, in the information model 120, with a rule that specifies the follow-up action), while the alert explicitly states the follow-up action to be taken. Therefore, in some embodiments, the generated alert includes data other than data explicitly included in the content of the document 104. Furthermore, other data within the alert may also take a different from than the form in which the data is represented within the document 104. For example, the recipient of the alert may be identified by role instead of by name (e.g., "notify the primary care physician of data associated with the patient" or "notify the nurse on call on the following time and date").

The method 200 includes manifesting the at least one alert to at least one user 230. In manifesting an alert, the system 100 executes functionality for providing any type of output to a user. In one embodiment, an alert manifestation engine 130 manifests the at least one alert to the at least one user. In another embodiment, the workflow application 150 manifests the alert. In some embodiments, the alert manifestation engine 130 manifests alerts and the workflow application 150 tracks a status of each alert, including, for example, whether or not the alert has been manifested and, for manifested alerts, the status of the follow-up action item. The system 100 (e.g., the alert manifestation engine 130 and/or the workflow application 150) may manifest the alert automatically, without human intervention.

The alert manifestation engine 130 may automatically generate an electronic message including the at least one alert, addressed to the at least one alert recipient. The alert manifestation engine 130 may automatically transmit the generated electronic message to the at least one alert recipient.

The alert manifestation engine 130 may automatically generate an electronic mail message including the at least one alert, addressed to the at least one alert recipient. The alert manifestation engine 130 may automatically transmit the generated electronic mail message to the at least one alert recipient.

The alert manifestation engine 130 may automatically generate a text message (e.g., an electronic message sent according to, for example, a Short Message Service protocol) including the at least one alert, addressed to the at least one alert recipient. The alert manifestation engine 130 may automatically transmit the generated text message to the at least one alert recipient.

In one embodiment, the workflow application 150 maintains a listing of documents 104 that include indications of follow-up actions. The workflow application 150 may maintain a list of recommendations associated with each such document 104. The workflow application 150 may maintain an identification of a location at which a procedure associated with the document 104 took place. The workflow application 150 may maintain one or more identifiers associated with the document 104 (e.g., encounter numbers). The workflow application 150 may maintain an identification of a reason for the underlying encounter associated with the document 104. The workflow application 150 may maintain name and/or contact information for at least one user associated with the indicated follow-up action. By way of example, in an embodiment in which the document 104 is a radiology-related document, the workflow application 150 may maintain a list of radiologist contact information, primary care physician contact information, and patient contact information; a healthcare personnel may monitor the lists and update as appropriate. The workflow application 150 may automatically create additional alerts via email or text to all intended recipients providing reminders of follow-up dates.

In some embodiments, the workflow application 150 maintains information associate with providers who treat a patient that is a subject of a document 104 but who treat the patient in a different context (e.g., potentially unrelated to the content of the document 104). In one of these embodiments, the workflow application 150 may determine that a follow-up action is required six months after generation of a document 104; the workflow application 150 may identify a provider who is already scheduled to interact with the patient, whether or not the provider treats the patient for anything related to the document 104. In another of these embodiments, the workflow application 150 may direct the sending of an alert to a provider, regardless of whether the provider sees the patient for any condition associated with the document 104, before the recommended date for the follow-up action to remind the provider to schedule the follow-up action.

The workflow application 150 may store a variety of data types with information relating to a document 104 including an indication of one or more follow-up actions. For example, the workflow application 150 may maintain a type of the indicated follow-up action. The workflow application 150 may maintain a type of underlying procedure (e.g., a procedure described in the document 104 giving rise to the follow-up recommendation). The workflow application 150 may maintain a status of the indicated follow-up action. The workflow application 150 may maintain a type of a procedure described by the content of the document 104, the procedure associated with the indicated follow-up action. The workflow application 150 may store a copy of the generated alert. The workflow application 150 may generate one or more additional tasks associated with the at least one alert. For example, if the alert reminds a physician to schedule an ultrasound for a patient within a time period, the workflow application 150 may generate a task for the physician to schedule the ultrasound appointment or to undertake a related task, such as discussing the ultrasound with the patient or providing a patient with the information needed to schedule an ultrasound appointment. The workflow application 150 may assign a generated task to an individual identified in data associated with the document 104 (e.g., identified in a value of the information model, identified in content of the document 104, or identified by a rule in the information model). The workflow application 150 may store an identification of a generated task and of an individual assigned the task, if any.

In contrast to a conventional workflow engine, the workflow application 150 may, automatically and without human input, generate a prioritized worklist that gives weight to the severity of a condition associated with the document 104, a type of alert, and a timing of an alert. By way of example, and without limitation, a follow-up CT lung screen for an incidental finding of a lung nodule has a higher priority than a routine chest X-ray. This workflow application 150, therefore, is not just a reminder system that generates reminders requested by human users, but part of an automated system that generates and manifests alerts according to a method targeted to implement standards of care.

In one embodiment, a radiology document 104 that has an implicit or explicit recommendation of follow up populates worklist in the workflow application 150; after follow up is completed, the document 104 and related information may be removed from the worklist and may be moved on to a separate worklist depending on the outcome of the review.

In one embodiment, the workflow application 150 may provide more than one worklist available via a drop-down list filtered by features of the document 104 or of the follow-up action item, such as, without limitation, date/type of procedure needed/primary contact.

In some embodiments, the method 200 includes automatically applying automatic speech recognition to an audio signal to produce a structured document representing contents of the audio signal. Referring now to FIG. 1B, the system 100 may include an automatic speech recognition system 160, used to generate a structured document 166 based on a user's speech. For example, the automatic speech recognition system 160 may include a structured document generator 164 receiving an audio signal via an I/O device (such as, for example, a microphone) and generating the structured document 166. As another example, the automatic speech recognition system 160 may generate an audio signal transcription 162 and provide the audio signal transcription 162 to the structured document generator 164 for generation of the structured document 166. The structured document 166 may include a plurality of portions (which may also be referred to as sub-templates, sub-portions or document components). Examples of techniques that may be used to create such structured documents may be found, for example, in commonly-owned U.S. Pat. No. 7,584,103, entitled, "Automated Extraction of Semantic Content and Generation of a Structured Document from Speech"; commonly-owned U.S. Pat. No. 7,716,040, entitled, "Verification of Extracted Data"; and the patents, patent applications, and other documents cited therein. These techniques, however, are merely examples of techniques that may be used to generate a structured document 166 based on speech, and do not constitute limitations of the present invention.

Once such a structured document 166 has been created, embodiments of the present invention may be used to automatically provide alerts to users of the system, such as to the speaker whose speech was recognized to create the structured document 166 and/or other users with whom the speaker may need to follow-up about content within the structured document 166.

Although depicted in FIG. 1B as executing within the computing device 101, which also provides document analysis functionality, the automatic speech recognition system 160 may be provided as a separate component in communication with the computing device 101.

Embodiments of the present invention have a variety of advantages. In some embodiments, an automated alert generator is improved by executing functionality to analyze content within a document (e.g., a document 104) in order to identify follow-up actions described within the document, implicitly or explicitly, and by automatically manifesting an alert including an indication of the follow-up action. In contrast to a system that could only generate alerts when explicitly instructed to do so, a system automatically executing functionality to identify implicit or explicit follow-up actions and electronically communicating related alerts to a target of the follow-up action provides improved technical functionality.

In other embodiments, implementation of the methods and systems described herein provide functionality for rapidly deploying changes in care guidelines. By way of example, deployment of a new care guideline may take tens of years to be generally known and acted upon but use of the methods and systems described herein provide technological improvements to such deployments through the identification, generation, and manifestation of alerts for actions described or mandated by care guidelines. Furthermore, such implementations provide technological solutions for the problem of how to implement reminder-generation technology without depending on human requests for reminders, especially in situations where individual interpretation of care guidelines or individual levels of awareness with standards of care may mean human requestors are unaware of a need for a follow-up action.

In further embodiments, implementation of the methods and systems described herein provide functionality with faster turnaround than a conventional system and providing timely and accurate delivery of alert manifestations. Additional such implementations are not limited to reminders requested by humans but automatically and without human input review documents to identify reminders that need to be generated but which humans did not request.

In one embodiment, implementation of the methods and systems described herein results in better patient care by creating an automated method for automatically generating and sending notifications to physicians and patients of recommended follow up. For example, if a patient sees a specialist, such as a radiologist, the specialist may prepare a report summarizing the visit or procedures and the report may include implicit or explicit recommendations for follow-up. In another embodiment, implementation of the methods and systems described herein results in facilitation of a radiologist's communication mandate and reduction in time spent by the radiologist in trying to reach a physician and/or a patient. In still another embodiment, implementation of the methods and systems described herein results in decreased human dependence (and, potentially, decreased human errors as a result) through the use of technology to recognize indications of follow-up actions and the automated creation of follow-up recommendations, and/or automated alerting.

Although the examples described herein pertain to interactions between radiologists, referring physicians, and patients, one of ordinary skill in the art will understand that the methods and systems described herein may be more broadly applied to any scenario in which two or more users may need to follow up with each other but risk failing to do so.

It is to be understood that although the invention has been described above in terms of particular embodiments, the foregoing embodiments are provided as illustrative only, and do not limit or define the scope of the invention. Various other embodiments, including but not limited to the following, are also within the scope of the disclosure. For example, elements and components described herein may be further divided into additional components or joined together to form fewer components for performing the same functions.

As used herein, "manifesting" data refers to providing output, to a user, that represents such data. Such output may take any form, such as a visual form and/or an auditory form. For example, such output may include any one or more of the following in any combination: text, graphics, images, video, and audio. As this description makes clear, any output described herein as being "manifested," may, for example, solely include text, solely include graphics, solely include video, or solely include audio.

The techniques described above may be implemented, for example, in hardware, software tangibly stored on a non-transitory computer-readable medium, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

A more detailed description is now provided of the computing devices and network environments with which the methods and systems described herein may be implemented. As will be understood by those of ordinary skill in the art, the follow descriptions provide embodiments of the types of computing devices and network environments which could be modified in order to enable the devices and environments to execute the innovative functionality described herein.

Figure 3A:
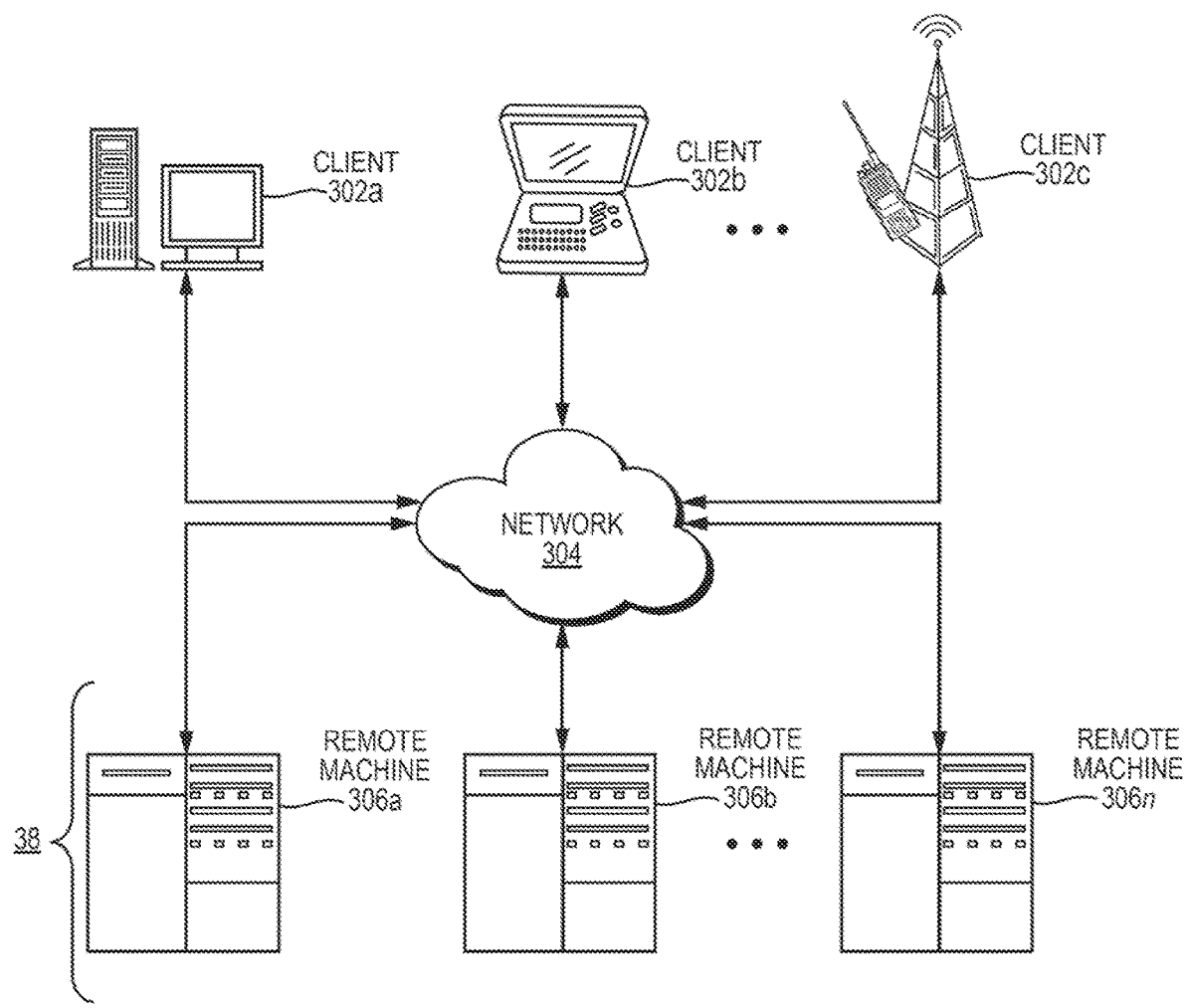
FIGS. 3A-3C are block diagrams depicting embodiments of computers useful in connection with the methods and systems described herein.

Referring now to FIG. 3A, an embodiment of a network environment is depicted. In brief overview, the network environment comprises one or more clients 302a-302n (also generally referred to as local machine(s) 302, client(s) 302, client node(s) 302, client machine(s) 302, client computer(s) 302, client device(s) 302, computing device(s) 302, endpoint(s) 302, or endpoint node(s) 302) in communication with one or more remote machines 306a-306n (also generally referred to as server(s) 306 or computing device(s) 306) via one or more networks 304.

Although FIG. 3A shows a network 304 between the clients 302 and the remote machines 306, the clients 302 and the remote machines 306 may be on the same network 304. The network 304 can be a local-area network (LAN), such as a company Intranet, a metropolitan area network (MAN), or a wide area network (WAN), such as the Internet or the World Wide Web. In some embodiments, there are multiple networks 304 between the clients 302 and the remote machines 306. In one of these embodiments, a network 304' (not shown) may be a private network and a network 304 may be a public network. In another of these embodiments, a network 304 may be a private network and a network 304' a public network. In still another embodiment, networks 304 and 304' may both be private networks.

The network 304 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. In some embodiments, the network 304 may comprise a wireless link, such as an infrared channel or satellite band. The topology of the network 304 may be a bus, star, or ring network topology. The network 304 may be of any such network topology as known to those ordinarily skilled in the art capable of supporting the operations described herein. The network 304 may comprise mobile telephone networks utilizing any protocol or protocols used to communicate among mobile devices, including AMPS, TDMA, CDMA, GSM, GPRS, or UMTS. In some embodiments, different types of data may be transmitted via different protocols. In other embodiments, the same types of data may be transmitted via different protocols.

A client 302 and a remote machine 306 (referred to generally as computing devices 300) can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communicating on any type and form of network and that has sufficient processor power and memory capacity to perform the operations described herein. A client 302 may execute, operate or otherwise provide an application, which can be any type and/or form of software, program, or executable instructions, including, without limitation, any type and/or form of web browser, web-based client, client-server application, an ActiveX control, or a JAVA applet, or any other type and/or form of executable instructions capable of executing on client 302.

In one embodiment, a computing device 306 provides functionality of a web server. In some embodiments, a web server 306 comprises an open-source web server, such as the APACHE servers maintained by the Apache Software Foundation of Delaware. In other embodiments, the web server executes proprietary software, such as the INTERNET INFORMATION SERVICES products provided by Microsoft Corporation of Redmond, Wash.; the ORACLE IPLANET web server products provided by Oracle Corporation of Redwood Shores, Calif.; or the BEA WEBLOGIC products provided by BEA Systems of Santa Clara, Calif.

In some embodiments, the system may include multiple, logically grouped, remote machines 106. In one of these embodiments, the logical group of remote machines may be referred to as a server farm 38. In another of these embodiments, the server farm 38 may be administered as a single entity.

Figure 3B:
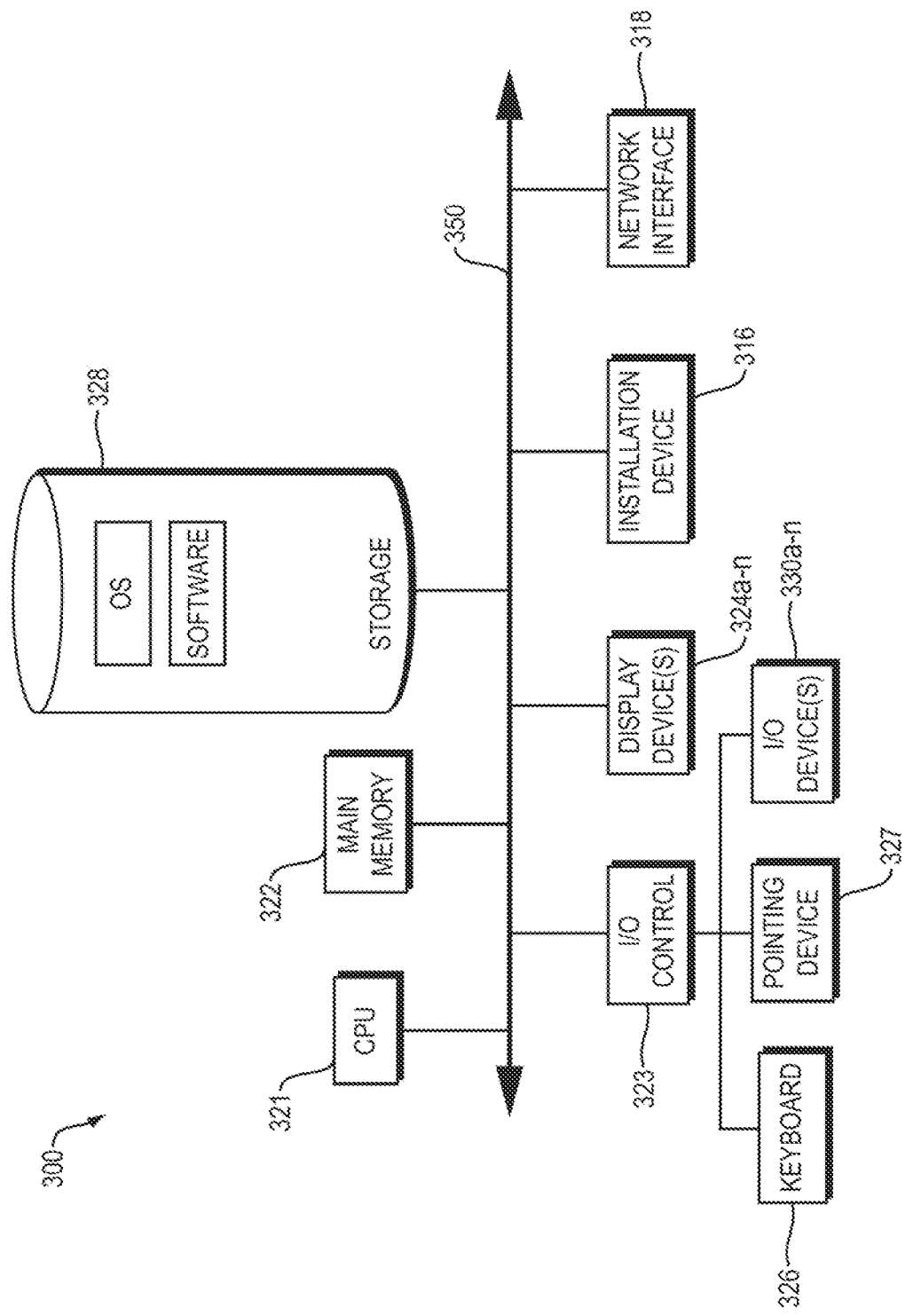
Figure 3C:
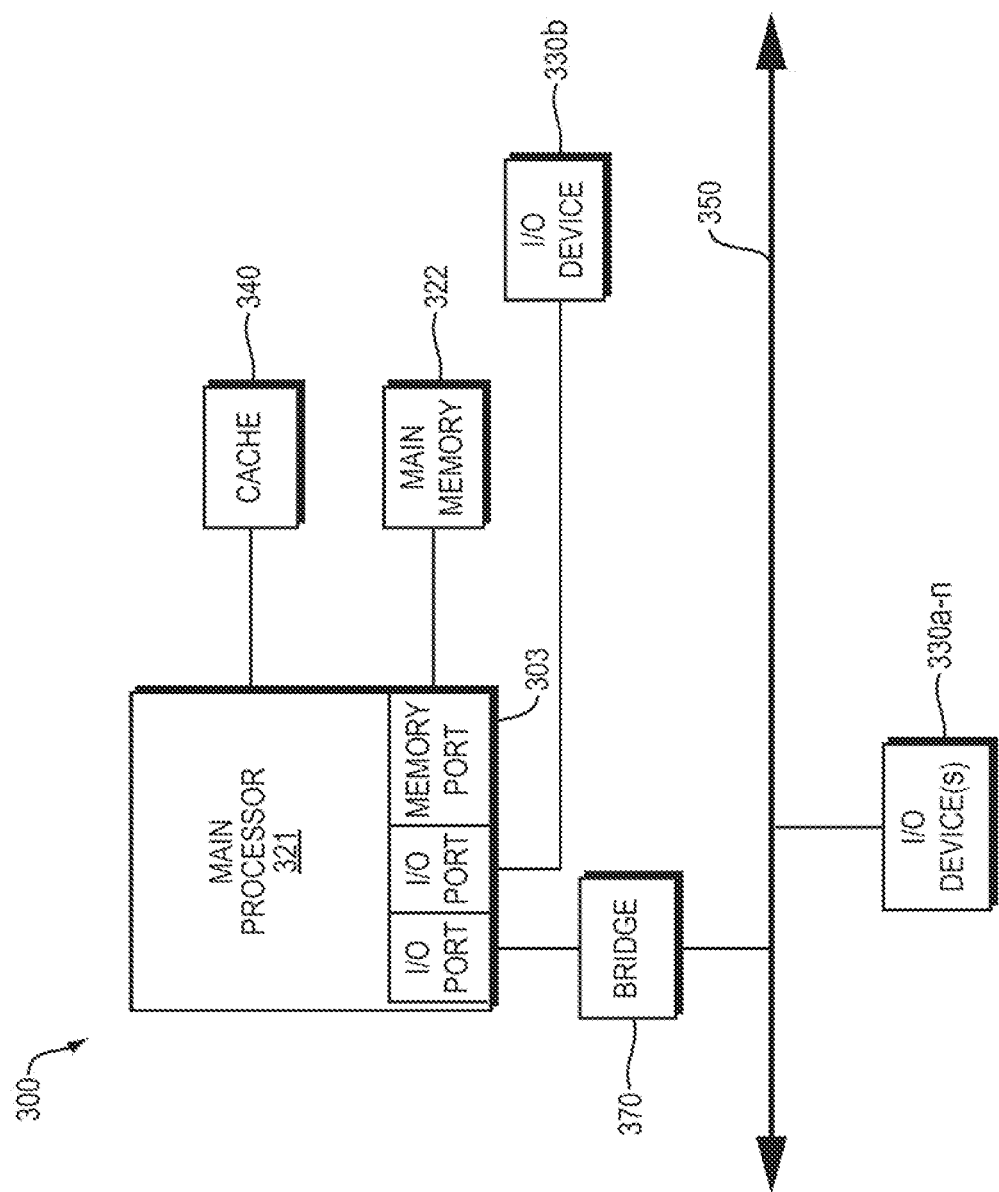

FIGS. 3B and 3C depict block diagrams of a computing device 300 useful for practicing an embodiment of the client 302 or a remote machine 306. As shown in FIGS. 3B and 3C, each computing device 300 includes a central processing unit 321, and a main memory unit 322. As shown in FIG. 3B, a computing device 300 may include a storage device 328, an installation device 316, a network interface 318, an I/O controller 323, display devices 324a-n, a keyboard 326, a pointing device 327, such as a mouse, and one or more other I/O devices 330a-n. The storage device 328 may include, without limitation, an operating system and software. As shown in FIG. 3C, each computing device 300 may also include additional optional elements, such as a memory port 303, a bridge 370, one or more input/output devices 330a-330n (generally referred to using reference numeral 330), and a cache memory 340 in communication with the central processing unit 321.

The central processing unit 321 is any logic circuitry that responds to and processes instructions fetched from the main memory unit 322. In many embodiments, the central processing unit 321 is provided by a microprocessor unit such as: those manufactured by Intel Corporation of Mountain View, Calif.; those manufactured by Motorola Corporation of Schaumburg, Ill.; those manufactured by International Business Machines of White Plains, N.Y.; or those manufactured by Advanced Micro Devices of Sunnyvale, Calif. The computing device 300 may be based on any of these processors, or any other processor capable of operating as described herein.

Main memory unit 322 may be one or more memory chips capable of storing data and allowing any storage location to be directly accessed by the microprocessor 321. The main memory unit 322 may be based on any available memory chips capable of operating as described herein. In the embodiment shown in FIG. 3B, the processor 321 communicates with main memory unit 322 via a system bus 350. FIG. 3C depicts an embodiment of a computing device 300 in which the processor communicates directly with main memory unit 322 via a memory port 303. FIG. 3C also depicts an embodiment in which the main processor 321 communicates directly with cache memory 340 via a secondary bus, sometimes referred to as a backside bus. In other embodiments, the main processor 321 communicates with cache memory 340 using the system bus 350.

In the embodiment shown in FIG. 3B, the processor 321 communicates with various I/O devices 330 via a local system bus 350. Various buses may be used to connect the central processing unit 321 to any of the I/O devices 330, including an ISA bus, an EISA bus, a PCI bus, a PCI-X bus, or a PCI-Express bus. For embodiments in which the I/O device is a video display device 324, the processor 321 may use an Advanced Graphics Port (AGP) to communicate with the display device 324. FIG. 3C depicts an embodiment of a computer 300 in which the main processor 321 also communicates directly with an I/O device 330b via, for example, HYPERTRANSPORT, RAPIDIO, or INFINIBAND communications technology.

A wide variety of I/O devices 330a-330n may be present in the computing device 300. Input devices include keyboards, mice, trackpads, trackballs, microphones, scanners, cameras, and drawing tablets. Output devices include video displays, speakers, inkjet printers, laser printers, and dye-sublimation printers. The I/O devices may be controlled by an I/O controller 323 as shown in FIG. 3B. Furthermore, an I/O device may also provide storage and/or an installation medium 316 for the computing device 300. In some embodiments, the computing device 300 may provide USB connections (not shown) to receive handheld USB storage devices such as the USB Flash Drive line of devices manufactured by Twintech Industry, Inc. of Los Alamitos, Calif.

Referring still to FIG. 3B, the computing device 300 may support any suitable installation device 316, such as a floppy disk drive for receiving floppy disks, a CD-ROM drive, a CD-R/RW drive, a DVD-ROM drive, tape drives of various formats, USB device, hard drive or any other device suitable for installing software and programs. The computing device 300 may further comprise a storage device, such as one or more hard disk drives or redundant arrays of independent disks, for storing an operating system and other software.

Furthermore, the computing device 300 may include a network interface 318 to interface to the network 304 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, IEEE 802.15.4, BLUETOOTH, ZIGBEE, CDMA, GSM, WiMax, and direct asynchronous connections). In one embodiment, the computing device 300 communicates with other computing devices 300' via any type and/or form of gateway or tunneling protocol such as Secure Socket Layer (SSL) or Transport Layer Security (TLS). The network interface 318 may comprise a built-in network adapter, network interface card, PCMCIA network card, card bus network adapter, wireless network adapter, USB network adapter, modem, or any other device suitable for interfacing the computing device 300 to any type of network capable of communication and performing the operations described herein.

In some embodiments, the computing device 300 may comprise or be connected to multiple display devices 324a-324n, of which each may be of the same or different type and/or form. As such, any of the I/O devices 330a-330n and/or the I/O controller 323 may comprise any type and/or form of suitable hardware, software, or combination of hardware and software to support, enable or provide for the connection and use of multiple display devices 324a-324n by the computing device 300. One ordinarily skilled in the art will recognize and appreciate the various ways and embodiments that a computing device 300 may be configured to have multiple display devices 324a-324n.

In further embodiments, an I/O device 330 may be a bridge between the system bus 350 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

A computing device 300 of the sort depicted in FIGS. 3B and 3C typically operates under the control of operating systems, which control scheduling of tasks and access to system resources. The computing device 300 can be running any operating system such as any of the versions of the MICROSOFT WINDOWS operating systems, the different releases of the UNIX and LINUX operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS CE, WINDOWS XP, WINDOWS 7, WINDOWS 8, WINDOWS 10, and WINDOWS VISTA, all of which are manufactured by Microsoft Corporation of Redmond, Wash.; MAC OS manufactured by Apple Inc. of Cupertino, Calif.; Red Hat Enterprise LINUX, a Linus-variant operating system distributed by Red Hat, Inc., of Raleigh, N.C.; or Ubuntu, a freely-available operating system distributed by Canonical Ltd. of London, England; or any type and/or form of a UNIX operating system, among others.

The computing device 300 can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein.

Having described certain embodiments of methods and systems for manifestation and transmission of follow-up notifications, it will now become apparent to one of skill in the art that other embodiments incorporating the concepts of the disclosure may be used. Therefore, the disclosure should not be limited to certain embodiments, but rather should be limited only by the spirit and scope of the following claims.

The invention claimed is:

1. A method for manifestation and transmission of follow-up notifications performed by at least one computer processor of a computing device, the method comprising:
   (A) determining whether a document indicates a follow-up action associated with content in the document, wherein determining further comprises:
   analyzing the content in the document;
   setting a value in the information model based on the analyzing;
   identifying one or more rules, within the information model, based on the value; and
   applying the rules to identify one or more explicit and one or more implicit follow-up actions within the document, wherein the one or more explicit and one or more implicit follow-up actions comprises a recommended procedure;
   (B) generating at least one alert including an indication of at least one of the explicit and implicit follow-up actions, wherein alerts pertaining to implicit follow-up actions includes data not explicitly included in the document;
   (C) manifesting the at least one alert to at least one user;
   (D) maintaining, by a workflow application, a listing of documents that include an indication of at least one follow-up action, the listing of documents including the document indicating the explicit and implicit follow-up actions and information associated with a provider treating a patient that is a subject of the document; and
   (E) before (C), directing, by the workflow application, sending of a second alert to the provider associated with the document, before a recommended date for manifesting the at least one alert to the at least one user.

2. The method of claim 1 further comprising applying automatic speech recognition to an audio signal to produce a structured document representing contents of the audio signal.

3. The method of claim 1, wherein determining further comprises applying the information model to determine whether the content in the document includes language associated with the follow-up action.

4. The method of claim 1, wherein determining further comprises applying the information model to determine whether the content in the document includes an identification of a recommended procedure associated with the follow-up action.

5. The method of claim 1, wherein determining further comprises applying the information model to determine whether the content in the document includes an identification of a date associated with the follow-up action.

6. The method of claim 1, wherein determining further comprises applying the information model to determine whether the content in the document includes an identification of a time associated with the follow-up action.

7. The method of claim 1, wherein determining further comprises applying, by a natural language processing engine, a machine learning model to content in the document to determine whether the content in the document includes language associated with the follow-up action.

8. The method of claim 1, wherein determining further comprises applying, by a natural language processing engine, a machine learning model to content in the document to determine whether the content in the document includes language associated with a finding implicitly indicating the follow-up action.

9. The method of claim 1, wherein generating further comprises:
(B-1) identifying at least one alert recipient;
(B-2) automatically generating an electronic message including the at least one alert; and
(B-3) automatically transmitting the generated electronic message to the at least one alert recipient.

10. The method of claim 9, wherein (B-2) further comprises automatically generating an electronic mail message.

11. The method of claim 9, wherein (B-2) further comprises automatically generating a text message.

12. The method of claim 1, wherein generating at least one alert further comprises assigning a date for the at least one alert on which to take the indicated follow-up action.

13. The method of claim 1 further comprising maintaining, by a workflow application, contact information for at least one user associated with the indicated follow-up action.

14. The method of claim 1 further comprising maintaining, by a workflow application, a type of the indicated follow-up action.

15. The method of claim 1 further comprising maintaining, by a workflow application, a status of the indicated follow-up action.

16. The method of claim 1 further comprising maintaining, by a workflow application, a type of a procedure described by the content of the document, the procedure associated with the indicated follow-up action.

17. The method of claim 1 further comprising storing, by a workflow application, the generated alert.

18. The method of claim 1 further comprises generating a task associated with the at least one alert.

19. The method of claim 1, wherein the document is a radiology report.

20. A non-transitory computer-readable medium storing computer program instructions executable by at least one computer processor to perform a method, the method comprising:
(A) determining whether a document indicates a follow-up action associated with content in the document, wherein determining further comprises:
analyzing the content in the document;
setting a value in the information model based on the analyzing;
identifying one or more rules, within the information model, based on the value; and
applying the rules to identify one or more explicit and one or more implicit follow-up actions within the document, wherein the one or more explicit and one or more implicit follow-up actions comprises a recommended procedure;
(B) generating at least one alert including an indication of at least one of the explicit and implicit follow-up actions, wherein alerts pertaining to implicit follow-up actions includes data not explicitly included in the document;
(C) manifesting the at least one alert to at least one user;
(D) maintaining, by a workflow application, a listing of documents that include an indication of at least one follow-up action, the listing of documents including the document indicating the explicit and implicit follow-up actions and information associated with a provider treating a patient that is a subject of the document; and
(E) before (C), directing, by the workflow application, sending of a second alert to the provider associated with the document, before a recommended date for manifesting the at least one alert to the at least one user.

* * * * *